US009681835B2

(12) United States Patent
Karmali et al.

(10) Patent No.: US 9,681,835 B2
(45) Date of Patent: Jun. 20, 2017

(54) DETECTION OF VESTIBULAR DISORDERS BASED ON VESTIBULAR NOISE

(75) Inventors: Faisal Karmali, Cambridge, MA (US); Csilla Haburcakova, Somerville, MA (US); Daniel Michael Merfeld, Lincoln, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 661 days.

(21) Appl. No.: 13/885,263

(22) PCT Filed: Nov. 15, 2011

(86) PCT No.: PCT/US2011/060684
§ 371 (c)(1),
(2), (4) Date: Jul. 3, 2013

(87) PCT Pub. No.: WO2012/068040
PCT Pub. Date: May 24, 2012

(65) Prior Publication Data
US 2013/0303939 A1 Nov. 14, 2013

Related U.S. Application Data

(60) Provisional application No. 61/413,794, filed on Nov. 15, 2010.

(51) Int. Cl.
*A61B 5/00* (2006.01)
*A61B 5/11* (2006.01)

(52) U.S. Cl.
CPC .......... *A61B 5/4023* (2013.01); *A61B 5/1116* (2013.01); *A61B 5/1128* (2013.01)

(58) Field of Classification Search
CPC ....... A61B 5/4863; A61B 5/11; A61B 5/1116; A61B 5/1124; A61B 5/1128; A61B 5/4023
See application file for complete search history.

(56) References Cited

U.S. PATENT DOCUMENTS

| 4,558,703 A | 12/1985 | Mark |
| 4,592,359 A | 6/1986 | Galbraith |
| 4,754,748 A | 7/1988 | Antowski |
| 5,658,322 A | 8/1997 | Fleming |
| 5,919,149 A | 7/1999 | Allum |

(Continued)

FOREIGN PATENT DOCUMENTS

| JP | 2007-268164 | 10/2007 |
| WO | WO 2004/045242 | 5/2004 |

(Continued)

OTHER PUBLICATIONS

International Search Report for International Application No. PCT/US2006/35759 dated Jul. 27, 2007, 3 pages.

(Continued)

*Primary Examiner* — Max Hindenburg
(74) *Attorney, Agent, or Firm* — Fish & Richardson P.C.

(57) ABSTRACT

A method for predicting whether a patient is afflicted by a vestibular disorder includes assaying vestibular noise; identifying a characteristic of the vestibular noise; and at least in part on the basis of the characteristic of the vestibular noise, providing information for predicting that a patient has a vestibular disorder.

36 Claims, 6 Drawing Sheets

(56) References Cited

U.S. PATENT DOCUMENTS

| | | | |
|---|---|---|---|
| 5,922,016 | A | 7/1999 | Wagner |
| 5,942,954 | A | 8/1999 | Galiana et al. |
| 5,951,596 | A | 9/1999 | Bellinger |
| 5,984,859 | A | 11/1999 | Lesinski |
| 6,063,046 | A | 5/2000 | Allum |
| 6,078,838 | A | 6/2000 | Rubinstein |
| 6,089,714 | A * | 7/2000 | Galiana .................. A61B 3/113 351/202 |
| 6,219,578 | B1 | 4/2001 | Collins et al. |
| 6,219,580 | B1 | 4/2001 | Faltys et al. |
| 6,295,472 | B1 | 9/2001 | Rubinstein et al. |
| 6,314,324 | B1 | 11/2001 | Lattner et al. |
| 6,358,272 | B1 | 3/2002 | Wilden |
| 6,430,443 | B1 | 8/2002 | Karell |
| 6,546,291 | B2 | 4/2003 | Merfeld et al. |
| 6,735,475 | B1 | 5/2004 | Whitehurst et al. |
| 6,748,275 | B2 | 6/2004 | Lattner et al. |
| 6,830,580 | B2 | 12/2004 | Neuberger |
| 6,921,413 | B2 | 7/2005 | Mahadevan-Jansen et al. |
| 7,225,028 | B2 | 5/2007 | Della Santina et al. |
| 7,285,099 | B1 | 10/2007 | Peterka |
| 7,488,341 | B2 | 2/2009 | Merfeld |
| 7,730,892 | B2 | 6/2010 | Merfeld et al. |
| 7,736,382 | B2 | 6/2010 | Webb et al. |
| 8,372,127 | B2 | 2/2013 | Merfeld |
| 2002/0072781 | A1 | 6/2002 | Lattner et al. |
| 2002/0151818 | A1 * | 10/2002 | Watt ..................... A61B 5/0496 600/552 |
| 2003/0105496 | A1 | 6/2003 | Yu et al. |
| 2003/0171787 | A1 | 9/2003 | Money et al. |
| 2003/0195588 | A1 | 10/2003 | Fischell et al. |
| 2004/0006287 | A1 | 1/2004 | Epley |
| 2004/0167415 | A1 | 8/2004 | Gelfland et al. |
| 2004/0199223 | A1 | 10/2004 | Andersen et al. |
| 2004/0215236 | A1 | 10/2004 | Lattner et al. |
| 2005/0201574 | A1 | 9/2005 | Lenhardt |
| 2005/0216072 | A1 | 9/2005 | Mahadevan-Jansen et al. |
| 2005/0222644 | A1 | 10/2005 | Killian et al. |
| 2005/0267549 | A1 | 12/2005 | Della Santina et al. |
| 2006/0004422 | A1 | 1/2006 | De Ridder |
| 2006/0079950 | A1 | 4/2006 | Lehnhardt et al. |
| 2006/0161227 | A1 | 7/2006 | Walsh et al. |
| 2006/0161255 | A1 | 7/2006 | Zarowski et al. |
| 2007/0012321 | A1 | 1/2007 | Zelinsky |
| 2007/0027405 | A1 | 2/2007 | Merfeld et al. |
| 2007/0027465 | A1 | 2/2007 | Merfeld et al. |
| 2007/0100263 | A1 | 5/2007 | Merfeld |
| 2007/0167985 | A1 | 7/2007 | Kirby |
| 2008/0172102 | A1 | 7/2008 | Shalev |
| 2011/0054356 | A1 | 3/2011 | Merfeld |

FOREIGN PATENT DOCUMENTS

| | | |
|---|---|---|
| WO | WO 2004/060015 | 7/2004 |
| WO | WO2009/129222 | 10/2007 |
| WO | WO2009/136935 | 11/2009 |
| WO | WO 2013/151773 | 10/2013 |

OTHER PUBLICATIONS

International Search Report for International Application No. PCT/US2006/028756, dated Jun. 30, 2008, 11 pages.
Notification Concerning Transmittal of the International Preliminary Report on Patentability for International Application No. PCT/US2006/028756, dated Mar. 19, 2009, 5 pages.
Notification Concerning Transmittal of International Preliminary Report on Patentability for International Application No. PCT/US2006/35759 dated Mar. 27, 2008, 6 pages.
Notification Concerning Transmittal of International Preliminary Report on Patentability for International Application No. PCT/US2006/027535 dated Feb. 7, 2008, 6 pages.
Written Opinion of the International Searching Authority for International Application No. PCT/US2006/027535, dated Jul. 25, 2007, 5 pages.
Benson et al., "Thresholds for the detection of the direction of whole-body, linear movement in the horizontal plane," Aviat Space Environ Med., 1986, 57:1088-96.
Benson et al., "Thresholds for the Reception of Whole Body Angular Movement About a Vertical Axis," Aviat Space Environ Med., Mar. 1989, 60:205-213.
Berg et al., "Deviance Information Criterion for Comparing Stochastic Volatility Models," J Business Economic Statistics, 2004, 22:107-120.
Bertolini et al., "Velocity storage contribution to vestibular self-motion perception in healthy human subjects," J Neurophysiol., 2011, 105:209-223.
Bielinski et al., "How Out-of-Level Testing Affects the Psychometric Quality of Test Scores," Nation Center on Educational Outcomes, Aug. 2000, 15 pages.
Bronstein et al., "Reduced self-motion perception in patients with midline Cerebellar lesions," Neuroreport, 2008, 19:691-693.
Burnham and Anderson, "Multimodel Inference: Understanding AIC and BIC in Model Selection," Sociological Meth Res., 2004, 33:261-304.
Celeux et al., Centre de recherche en Economie et,statistique (2003) "Deviance information criteria for missing data models," INSEE, Paris, 30 pages.
Clark and Graybiel, "Perception of the postural vertical in normals and subjects with labyrinthine defects," J Exp Psychol., 1963, 65:490-494.
Cohen et al., "Spatial orientation of the angular vestibule-ocular reflex," J Vestib Res., 1999, 9:163-172.
Cohen et al., "Velocity storage, nystagmus, and visual-vestibular interactions in humans," Ann NY Acad Sci., 1981, 374:421-33.
Crane and Demer, "Human Horizontal Vestibulo-Ocular Reflex Initiation: Effects of Acceleration, Target Distance, and Unilateral Deafferentation," J Neurophysiology, 1998, 80:1151-1166.
Crane, "Fore-ail translation aftereffects," Exp Brain Res., 2012, 219:477-487.
Diekmann et al., "Maintaining spatial body alignment on a rotating platform by means of active counter-circling: role of vestibular and podokinesthetic afferent," Exp Brain Res., 2004, 158:504-518.
Dimitri et al., "Multivariate vestibular testing: laterality of unilateral Meniere's disease," J Vestib Res., 2001, 11:405-412.
Fernandez and Goldberg, "Physiology of peripheral neurons innervating otolith organs of the squirrel monkey. III. Response Dynamics," J Neurophysiol., 1976, 39:996-1008.
Firth, "Bias reduction of maximum likelihood estimates," Biometrika, 1993, 80:27-38.
Foster and Bischof, "Thresholds from psychometric functions: superiority of bootstrap to incremental and probit variance estimators," Psychol Bull., 1991, 109:152-159.
Goldberg and Fernandez, "Physiology of peripheral neurons innervating semicircular canals of the squirrel monkey. I. Resting discharge and response to constant angular accelerations," J Neurophysiol., 1971b, 34:635-60.
Goldberg and Feruandez, "Physiology of peripheral neurons innervating semicircular canals of the squirrel monkey. III. Variations among units in their discharge properties," J Neurophysiol., 1971a, 34:676-84.
Golding, "Motion sickness susceptibility questionnaire revised and its relationship to other forms of sickness," Brain Res Bulletin, 1998, 47:507-16.
Gong et al. "Prototype Neural Semicircular Canal Prosthesis Using Patterned Electrical Stimulation," Annals Biomed Engineering, 2000, 28:572-58.
Gong et al., "System Design and Performance of a Unilateral Horizontal Semicircular Canal Prosthesis" IEEE Transactions on Biomedical Engineering, Feb. 2002, 49(2):175-181.
Grabherr et al., "Vestibular thresholds for yaw rotation about an earth-vertical axis as a function of frequency," Exp Brain Res., Apr. 2008, 186(4):677-681.
Graybiel et al., "The law of the otolith organs," Fed Proc., 1946, 5:35.

(56) References Cited

OTHER PUBLICATIONS

Green and Angelaki, "Resolution of sensory ambiguities for gaze stabilization requires a second neural integrator," J Neurosci., 2003, 23:9265-9275.
Haburcakova et al., "Frequency dependence of vestibuloocular reflex thresholds," J Neurophysiol., 2012, 107:973-983.
Hall, "Hybrid adaptive procedure for estimation of psychometric functions," J Acoust Soc Am., 1981, 69:1763-1769.
Ifediba et al., "The role of 3-canal biomechanics in angular motion transduction by the human vestibular labyrinth," Ann Biomed Eng., 2007, 35:1247-63.
Jakel and Wichmann, "Spatial tour-alternative forced-choice method is the preferred psychophysical method for naive observers," J Vis., 2006, 6:1307-1322.
Kaernbach, "Slope bias of psychometric functions derived from adaptive data," Percept Psychophys, 2001, 63:1389-1398.
Klein, "Measuring, estimating, and understanding the psychometric function: a commentary," Percept Psychophys, 2001, 63:1421-1455.
Knoblauch and Maloney, "Estimating classification images with generalized linear and additive models," J Vis., 2008, 8:1-19.
Kosmidis, "Bias reduction in exponential family nonlinear models," PhD, thesis, Dept. of Statistics, Univ, Warwick, England, 2007, 160 pages.
Leek MR, "Adaptive procedures in psychophysical research," Percept Psychophys, 2001, 63:1279-92.
Leek et al., "Estimation of psychometric functions from adaptive procedures," Percept Psychophys, 1992, 51:247-256.
Lim et al., "Self-motion direction-detection thresholds for whole body roll tilts about an earth-horizontal axis," ARO, 2009, Abstr 103, Session D15: Poster, 1 page.
Lim and Merfeld, "Signal Detection Theory and Vestibular Perception: II, Fitting Perceptual Thresholds as a Function of Frequency," Exp Brain Res., 2012, 222:303-320.
Lim and Merfeld, "Erratum to: Signal Detection Theory and Vestibular Perception: II, Fitting Perceptual Thresholds as a Function of Frequency," Exp Brain Res., 2013, 224:501.
Mann et al., "The perception of the vertical; visual and non-labyrinthine cues," J Exp Psychol., 1949, 39:538-547.
McKee et al., "Statistical properties of forced-choice psychometric functions: Implications of probit analysis," Atten Percept Psychophys, 1985, 37:286-298.
Merfeld, "Signal detection theory and vestibular thresholds: 1. Basic theory and practical considerations," Exp Brain Res., 2011, 210:389-405.
Merfeld et al., "Vestibular perception and action employ qualitatively different mechanisms. I. Frequency response of VOR and perceptual responses during Translation and Tilt," J Neurophysiol., 2005a, 94:186-98.
Merfeld et al., "Vestibular perception and action employ qualitatively different mechanisms. II. VOR and perceptual responses during combined Tilt & Translation," J Neurophysiol., 2005b, 94:199-205.
Merfeld et al. "Ch. 7.7—*Vestibular Prosthetics*". Neuroprosthetics: Theory and Practice, K. Horch and G. Dhillon, Editors. 2002, 32 pages.
MOOG Systems Group. Series 6DOF2000E Electric Motion Platform. 2 pages, Feb. 2008.
Morgan et al., "Observers can voluntarily shift their psychometric functions without losing sensitivity," Atten Percept Psychophys., 2012, 74:185-193.
Neuhauser et al., "The interrelations of migraine, vertigo and migrainous vertigo," Neurol., 2001, 56:436-441.
Okada et al., "Vestibular perception of angular velocity in normal subjects and in patients with congenital nystagmus," Brain, 1999, 122 (Pt 7):1293-1303.
Peterka et al., "Age-related changes in human vestibulo-ocular and optokinetic reflexes: pseudorandom rotation tests," J Vestib Res., 1990, 1:61-71.
Raphan et al., "Velocity storage in the vestibulo-ocular reflex arc (VOR)," Exp Brain Res., 1979, 35:229-48.
Roditi and Crane, "Directional asymmetries and age effects in human self-motion perception," J Assoc Res Otolaryngol., 2012, 13:381-401.
Roditi and Crane, "Suprathreshold asymmetries in human motion perception," Exp Brain Res., 2012, 219:369-379.
Sinha et al., "Perception of self motion during and after passive rotation of the body around an earth-vertical axis," Prog Brain Res., 2008, 171:277-281.
Soyka et al., "Modeling direction discrimination thresholds for yaw rotations around an earth-vertical axis for arbitrary motion profiles," Exp Brain Res., 2012, 220:89-99.
Soyka et al., "Predicting direction detection thresholds for arbitrary translational acceleration profiles in the horizontal plane," Exp Brain Res., 2011, 209:95-107.
Taylor and Creelman, "PEST: Etlicient estimates on probability functions," J Acoust Soc Am., 1967, 41:782-787.
Treutwein and Strasburger, "Fitting the psychometric function," Percept Psychophys., 1999, 61:87-106.
Wall et al. "Vestibular Function and Anatomy". Department of Otolaryngology—Head and Neck Surgery, University of Texas Medical Branch, Galveston, TX, 1998, pp. 1891-1901.
Wall et al. "Vestibular Prostheses: the Engineering & Biomedical Issues," J Vestibular Res., 2002, 11:1-19.
Walsh, "Role of the vestibular apparatus in the perception of motion on a parallel swing," J Physiol., 1961, 155:506-513.
Wedderburn, "On the existence and uniqueness of the maximum likelihood estimates for certain generalized linear models," Biometrika, 1976, 63:27-32.
Wells et al. "Optical stimulation of neural tissue in vivo". Optics Letters, Mar. 2005, 30(5):504-506.
Wichmann and Hill, "The psychometric function: I. Fitting, sampling, and goodness of fit," Percept Psychophys., 2001a, 63:1293-1313.
Wichmann and Hill, "The psychometric function: II. Bootstrap-based confidence intervals and sampling," Percept Psychophys., 2001b, 63:1314-1329.
'Wikipedia' [online] "Maximum likelihood," May 2014, [retrieved on Jun. 2, 2014]. Retrieved from the Internet: http://en.wikipedia,org/wiki/Maximum likelihood#Higher-order-.properties, 14 pages.
Yssaad-Fesselier and Knoblauch, "Modeling psychometric functions R," Behav Res Methods, 2006, 38:28-41.
Zupan and Merfeld, "Interaural self-motion linear velocity thresholds are shifted by roll vection," Exp Brain Res., 2008, 191:505-11.
International Search Report and Written Opinion for PCT/US2011/060684 dated Jun. 28, 2012.

\* cited by examiner

DETECTION OF VESTIBULAR DISORDERS BASED ON VESTIBULAR NOISE

RELATED APPLICATIONS

This application is a 371 U.S. national stage application of PCT/US2011/060684, filed Nov. 15, 2011, which claims the benefit of the priority date of U.S. Provisional Application 61/413,794, filed on Nov. 15, 2010, the contents of which are herein incorporated by reference.

STATEMENT OF GOVERNMENT RIGHTS

This invention was made with government support under Grant R01-DC 04158 awarded by NIH/NIDCD. The government has certain rights in the invention.

TECHNICAL FIELD

This invention relates to the vestibular system, and in particular, to the diagnosis of vestibular dysfunction.

BACKGROUND

The vestibular system of the inner ear enables one to perceive body position and movement. In an effort to assess the integrity of the vestibular system, it is often useful to test its performance. Such tests are often carried out at a vestibular clinic.

Vestibular clinics typically measure reflexive responses like balance or the vestibulo-ocular reflex to diagnose a subject's vestibular system. The vestibulo-ocular reflex ("VOR") is one in which the eyes rotate in an attempt to stabilize an image on the retina. Since the magnitude and direction of the eye rotation depend on the signal provided by the vestibular system, observations of eye rotation provide a basis for inferring the state of the vestibular system.

In typical measurements, one stimulates the vestibular system multiple times and observes the resulting VOR. This results in a set of VOR measurements that are then processed to eliminate the harmful effects of noise in the measurements. The resulting averaged VOR data, once as much noise as possible has been removed, provides a basis for predicting whether or not a vestibular disorder exists.

SUMMARY

The invention is based on the recognition that vestibular noise offers a basis for diagnosing the existence of vestibular dysfunction.

In one aspect, the invention features a method for providing information for predicting that a patient has a vestibular disorder. Such a method includes assaying vestibular noise; identifying a characteristic of the vestibular noise; and at least in part on the basis of the characteristic of the vestibular noise, providing information for predicting that a patient has a vestibular disorder.

In some practices, assaying vestibular noise includes measuring the patient's VOR. Among these practices are those in which measuring the patient's VOR includes measuring VOR during patient movement, and those in which measuring the patient's VOR includes measuring VOR while the patient stares fixedly at a target.

Other embodiments include those in which assaying vestibular noise includes receiving information indicative of a patient's perception of motion.

Among the practices that include receiving information indicative of a patient's perception of motion are those in which the information indicative of a patient's perception of motion comprises information indicative of perceived direction of motion, and those in which information indicative of a patient's perception of motion comprises information representing a selection from among two or more alternatives.

Examples of a selection between alternatives include selection from the group consisting of motion in a first direction and motion in a second direction, a selection of an alternative selected from the group consisting of a perception of motion and a perception of motionlessness, a selection of an alternative selected from the group consisting of a perception of motion and a perception of motionlessness, a selection from the group consisting of a first time interval and a second time interval, wherein a feature of interest occurs in the first time interval and the feature is absent from the second time interval, a selection from the group consisting of a first time interval and a second time interval, wherein the motion in the first interval has a larger amplitude than the motion in the second interval, and a selection from the group consisting of a first time interval and a second time interval, wherein the motion in the first interval has a lower frequency than the motion in the second interval.

Alternative practices rely on different characteristics of the vestibular noise, such as the likelihood that the patient will perceive motion, the noise amplitude of the vestibular noise, the frequency dependence of the noise, and the variability of the noise. Patient perception is related to vestibular noise. Accordingly, other practices rely on the patient's perception.

Practices of the invention also vary on the information to be provided for use in predicting that a patient has a vestibular disorder. For example, in some practices, the information indicates a slope of a curve that relates a likelihood that a particular motion will cause a VOR having a specified characteristic with a characteristic of the particular motion. In other practices, the information indicates a shape of a curve that relates a likelihood that a particular motion will cause a VOR having a specified characteristic with a characteristic of the particular motion. In yet other embodiments, the information indicates a bias in a curve that relates a likelihood that a particular motion will cause a VOR having a specified characteristic with a characteristic of the particular motion. In yet other embodiments, the information indicates variance of the vestibular noise.

In other practices, the information provided relates to patient perception. Among these practices are those in which the information indicates a slope of a curve that relates a likelihood that a particular motion will be perceived by a patient with a characteristic of that motion, those in which the information indicates a shape of a curve that relates a likelihood that a particular motion will be perceived by the patient with a characteristic of that motion, and those in which the information indicates a bias in a curve that relates a likelihood that a particular motion will be perceived by a patient with a characteristic of the particular motion.

Among the practices of the invention are those in which the vestibular disorder is one from the group consisting of bilateral vestibular hypofunction, unilateral vestibular loss, perilymphatic fistula, post-traumatic vertigo, Meniere's syndrome, migraine associated dizziness, Semicircular canal dehiscence, vestibular loss due to ototoxicity, and labyrinthitis.

In some practices, measuring vestibular noise includes causing a patient to experience a set of motions, each of the motions in the set of motions causing the patient to experience a VOR; for each motion in the set of motions, measuring the patient's VOR, thereby generating a plurality of VOR measurements; on the basis of the VOR measurements, estimating a likelihood that a particular motion will cause the patient to experience a VOR having a specified VOR characteristic; and based on the likelihood, providing information for predicting that a patient has a vestibular disorder.

Among the foregoing practices are those in which causing a patient to experience a set of motions includes causing the patient to experience a motion having a specified velocity profile and a specified duration, an/or motion having random characteristics, and/or motion having a sinusoidal velocity profile, and or motion at different frequencies. In the latter case, the information for predicting whether a patient has a vestibular disorder includes providing information indicative of frequency dependence of the vestibular noise.

In another practice of the invention, measuring vestibular noise includes causing a patient to experience a set of motions, at least some of the motions in the set of motions causing the patient to experience a perception; for each motion in the set of motions, receiving information indicative of whether a patient has perceived motion, thereby generating a plurality of perception measurements; on the basis of the perception measurements, estimating a likelihood that a particular motion will cause the patient to experience a perception having a specified characteristic; and based on the likelihood, providing information for predicting that a patient has a vestibular disorder.

In another aspect, the invention features a non-transitory computer-readable medium having encoded thereon software for causing a computer to execute any of the foregoing methods In yet another aspect, the invention features a system for estimating a likelihood of vestibular dysfunction. Such a system includes means for assaying vestibular noise; means for executing computer-readable instructions for determining, at least in part on the basis of the vestibular noise, a likelihood of vestibular dysfunction; and tangible non-transitory means for storing the instructions.

In another aspect, the invention features an apparatus for providing information to by used in predicting whether a patient is afflicted by a vestibular disorder. Such an apparatus includes a motion platform for moving the patient; a controller for controlling motion of the motion platform; a sensor for detecting a signal indicative of the patient's vestibular noise; and a processor configured to extract, from the signal, a characteristic of the patient's vestibular noise, and to provide, based at least in part on the characteristic, information for use in predicting whether the patient is afflicted by a vestibular disorder.

In some embodiments, the sensor includes a VOR sensor for measuring the patient's VOR.

Other embodiments include a target disposed to enable the patient to stare fixedly thereon, either during motion of the motion platform and/or when the platform is stationary.

Among the embodiments are those in which sensor includes a signaling device operated by the patient to provide information indicating the patient's perception of motion. Examples of signaling devices are those configured to enable the patient to indicate a perceived direction of motion and those configured to enable the patient to provide information indicating a selection from among two or more alternatives. The range of alternatives is broad and encompasses information representing a selection from the group consisting of motion in a first direction and motion in a second direction, and information representing a selection between a perception of motion and a perception of motionlessness.

In some embodiments, the signaling device is configured to enable the patient to indicate a selection from a group consisting of a first time interval and a second time interval, wherein a feature of interest occurs in the first time interval and the feature is absent from the second time interval. In others, the signaling device is configured to enable the patient to indicate a selection from a group consisting of a first time interval and a second time interval, wherein the motion in the first interval has a larger amplitude than the motion in the second interval. And in yet others, the signaling device is configured to enable the patient to indicate a selection from a group consisting of a first time interval and a second time interval, wherein the motion in the first interval has a lower frequency than the motion in the second interval.

Additional embodiments of the apparatus include those in which the processor is configured to extract, from the signal, a likelihood that the patient will perceive motion, those in which the processor is configured to extract, from the signal, a noise amplitude, those in which the processor is configured to extract, from the signal, information indicative of a frequency dependence of the vestibular noise, those in which the processor is configured to extract, from the signal, information indicative of a frequency dependence of the patient's perception, and those in which the processor is configured to extract, from the signal, information indicative of variability of the vestibular measurement.

In other embodiments, the controller causes the motion platform to execute a set of motions; and for each for each motion in the set of motions, the sensor measures the patient's VOR, thereby generating a plurality of VOR measurements. The processor, in these embodiments is configured to estimate, at least in part on the basis of the VOR measurements, a likelihood that a particular motion will cause the patient to experience a VOR having a specified VOR characteristic; and based at least in part on the likelihood, to provide information for predicting that a patient is afflicted by a vestibular disorder.

Also among the embodiments are those in which the controller causes the motion platform to perform a set of motions and wherein for each motion in the set of motions, the sensor receives information indicative of whether a patient has perceived motion, thereby generating a plurality of perception measurements. In these embodiments, the processor is configured to estimate, at least in part on the basis of the perception measurements, a likelihood that a particular motion will cause the patient to experience a perception having a specified characteristic; and based at least in part on the likelihood, provides information for predicting that a patient is afflicted by a vestibular disorder.

In some of these embodiments, the processor uses, as a specified characteristic of the VOR, movement of the eye in a direction opposed to a direction of the motion. Also included among the embodiments are those in which the controller causes the motion platform to execute a set of motions having specified velocity profiles and a specified durations, those in which the controller causes the motion platform to execute motions having random characteristics, and those in which the controller causes the motion platform to execute motions having a sinusoidal velocity profile.

In some embodiments, the processor is configured to provide information indicative of a slope of a curve that relates a likelihood that a particular motion will cause a VOR having a specified characteristic with a characteristic of the particular motion. In others, the processor is configured to provide information indicative of a shape of a curve that relates a likelihood that a particular motion will cause a VOR having a specified characteristic with a characteristic of the particular motion. In still others, the processor is configured to provide information indicative of a bias in a curve that relates a likelihood that a particular motion will cause a VOR having a specified characteristic with a characteristic of the particular motion.

Still other embodiments include those in which the processor is configured to provide information indicative of a slope of a curve that relates a likelihood that a particular motion will be perceived by a patient with a characteristic of the particular motion, those in which the processor is configured to provide information indicative of a shape of a curve that relates a likelihood that a particular motion will be perceived by the patient with a characteristic of the particular motion, and those in which processor is configured to provide information indicative of a bias in a curve that relates a likelihood that a particular motion will be perceived by a patient with a characteristic of the particular motion, and those in which the processor is configured to provide information indicative of variance of the vestibular noise.

Additional embodiments include those in which the controller is configured to cause the motion platform to execute different motions at different frequencies. In these embodiments, the processor is configured to provide information indicative of frequency dependence of the vestibular noise.

The processor can also be configured to provide information for predicting that a patient is afflicted by any one of a number of conditions, including vestibular hypofunction, unilateral vestibular loss, perilymphatic fistula, post-traumatic vertigo, Meniere's syndrome, migraine associated dizziness, semicircular canal dehiscence, vestibular loss due to ototoxicity, and labyrinthitis, or any combination thereof.

These and other features of the invention will be apparent from the following detailed description, the appendices, and the accompanying drawings, in which:

DETAILED DESCRIPTION

Figure 1:
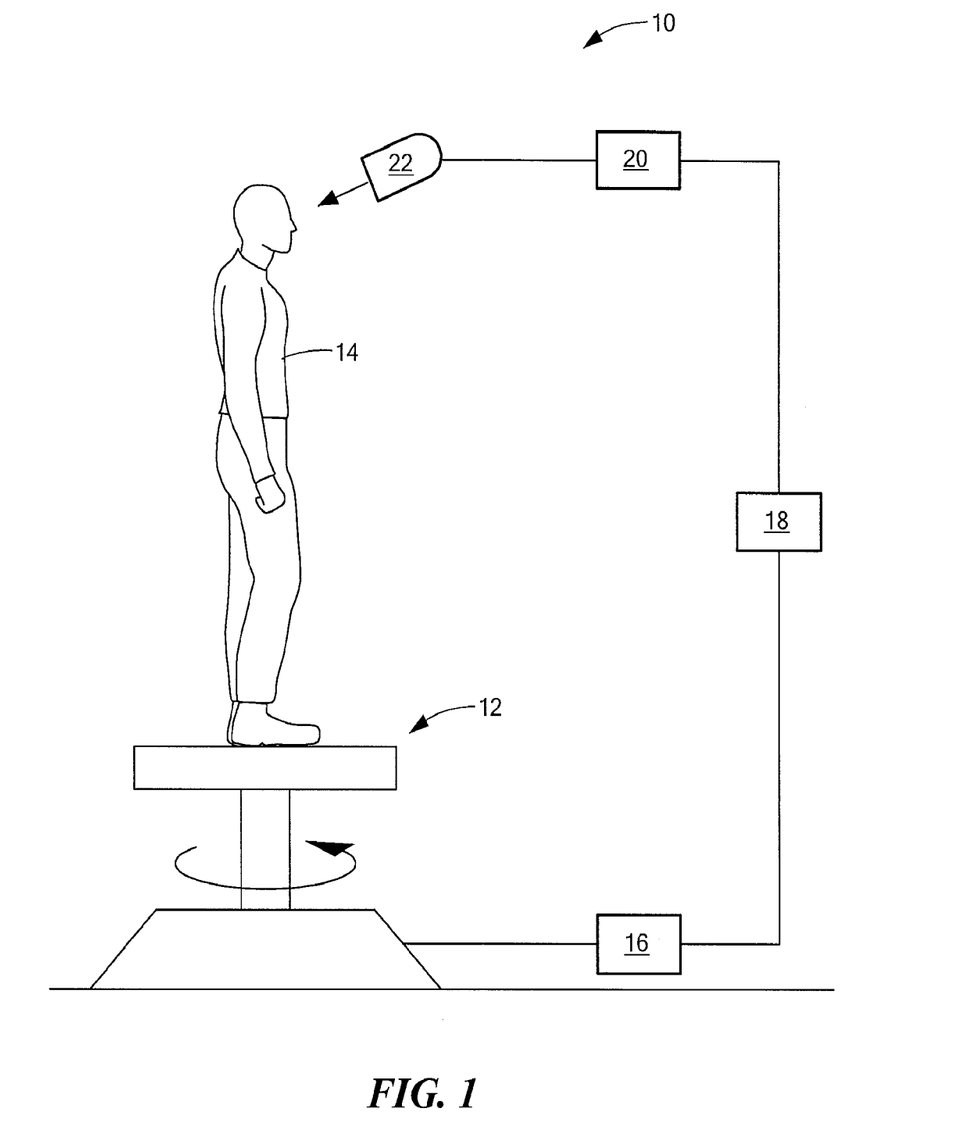
FIG. 1 shows one system for carrying out the methods disclosed herein.

A system 10 configured for using sensory noise to assist in prediction of the existence of a vestibular disorder as described herein includes a motion platform 12 that moves a subject 14 according to a motion set. Examples of a suitable motion platform include a Barany rotator for yaw motion, and a Moog 6 DOF motion platform for pitch, roll, and yaw, as well as for translation along each of three axes. An alternative motion platform 12 would be one that translates the subject 14 in one, two, or three dimensions and/or rotates the subject in one, two, or three dimensions.

The motion platform 12 is under control of a motion controller 16 that can be controlled either manually or by a computer 18, either internal to or external to the motion controller 16. In some embodiments, such a computer would have access to a non-transitory computer-readable medium having encoded thereon software for causing the computer 18 to carry out the tasks described herein.

A motion set consists of several motions that occur one after another. Each motion is characterized by its own motion profile. A motion profile describes the evolution of the motion over time. For instance, a motion might be characterized by certain motion profile parameters, such as positional amplitude, velocity amplitude, frequency, direction, whether the motion changes velocity amplitude, how quickly it changes amplitude, whether it changes sinusoidally, linearly, or according to some other functional form. A motion set might includes different motions with different motion profiles, or multiple occurrences of the same motion. In some embodiments, motions are arranged randomly within a motion set to prevent adaptation and prediction by the subject 14 from distorting the results.

The system 10 further may include a VOR detector 20 configured to capture data representing the VOR response of a subject 14. Many such VOR detectors are known, including semi-invasive detectors, such as coils that are implanted in the eye, and non-invasive detectors, such as coils embedded in contact lenses that are placed on the eye, cameras 22 or machine vision systems that detect eye movement, and electro-oculographic systems.

In operation, the subject 14 is placed on the motion platform 12 and the VOR detector 22 is configured to capture the subject's VOR. Then, the motion platform 12 moves the subject 14 according to a motion set having multiple motions. During each motion, the VOR detector 20 detects the subject's VOR response and provides it to the computer 18. The computer 18 then correlates the VOR response with the particular motion profile that stimulated the VOR.

Figure 2:
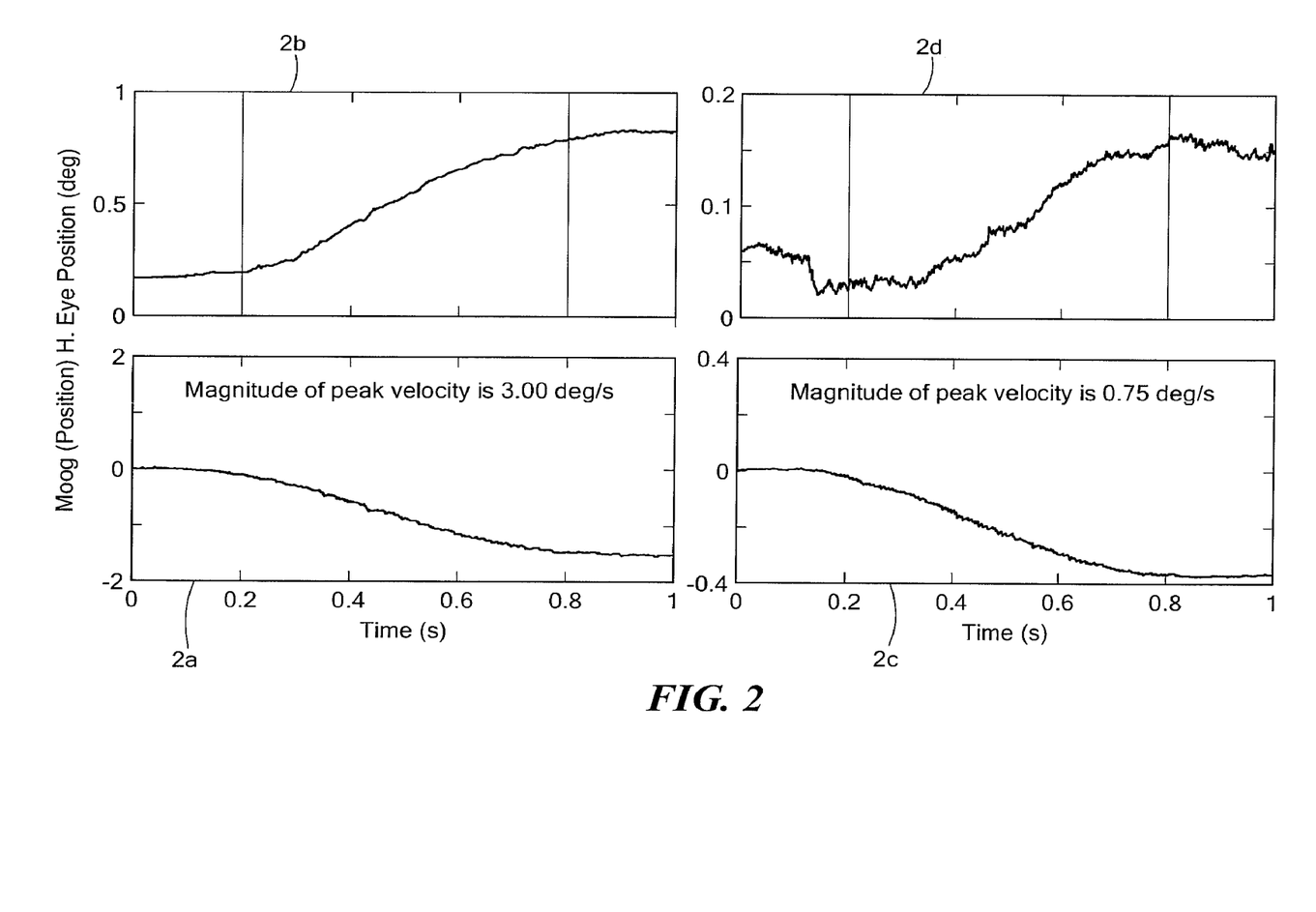
FIG. 2 shows VOR responses for different motion profiles.

In general, a motion set is selected to have a mixture of motions, some of which have small velocities and others of which have large velocities. Each motion in the motion set causes a particular VOR. For example, in FIG. 2, plot 2a shows a motion lasting one second and having a sinusoidal position profile and a maximum velocity, between 0.4 and 0.6 seconds, of 3 degrees per second. This results in a corresponding VOR in which the eye moves in the opposite direction, as shown in plot 2b. Plot 2c shows a similar motion profile, but with a maximum velocity of only 0.75 degrees per second. As shown in plot 2d, the corresponding VOR still shows eye movement in the correct direction, but with considerably more noise. A comparison between the vertical axes of plot 2d and plot 2b also shows that the extent of the eye movement is significantly reduced.

It is apparent from FIG. 2 that as the velocity decreases further, there will come a point where the movement of the eye is dominated not so much by the vestibular system but by random noise. To the extent this noise originates in the vestibular system, it is sensory noise, the characteristics of which contain information about the condition of the vestibular system. Such noise will therefore be referred to herein as "vestibular noise."

Vestibular noise tends to cause the signal-to-noise ratio of the vestibular system's output to the brain to be outside a range that is optimal. As a result, vestibular noise is believed to impact the patient's behavior, including both perception and reflexive responses. For example, when the vestibular noise level is too high compared to the vestibular signal level, the signal-to-noise ratio will be below the range that is optimal for behavior, whereas when the vestibular noise level is too low compared to the vestibular signal level the signal-to-noise ratio will be above the range that is optimal for behavior.

As the motion platform 12 causes the subject 14 to undergo different motions with different peak velocities, it is possible to gather statistics that indicate how likely it is, for a given velocity, that the subject's eye will move in a direction consistent with the direction in which the motion platform 12 moves the subject 14. These statistics can be represented as a likelihood graph, such as that shown in FIG. 3. The overall shape of the likelihood graph thus depends largely on characteristics of vestibular noise, and is therefore itself a characteristic of vestibular noise. For example, in the absence of any vestibular noise whatsoever, the likelihood graph would approach a step function.

Figure 3:
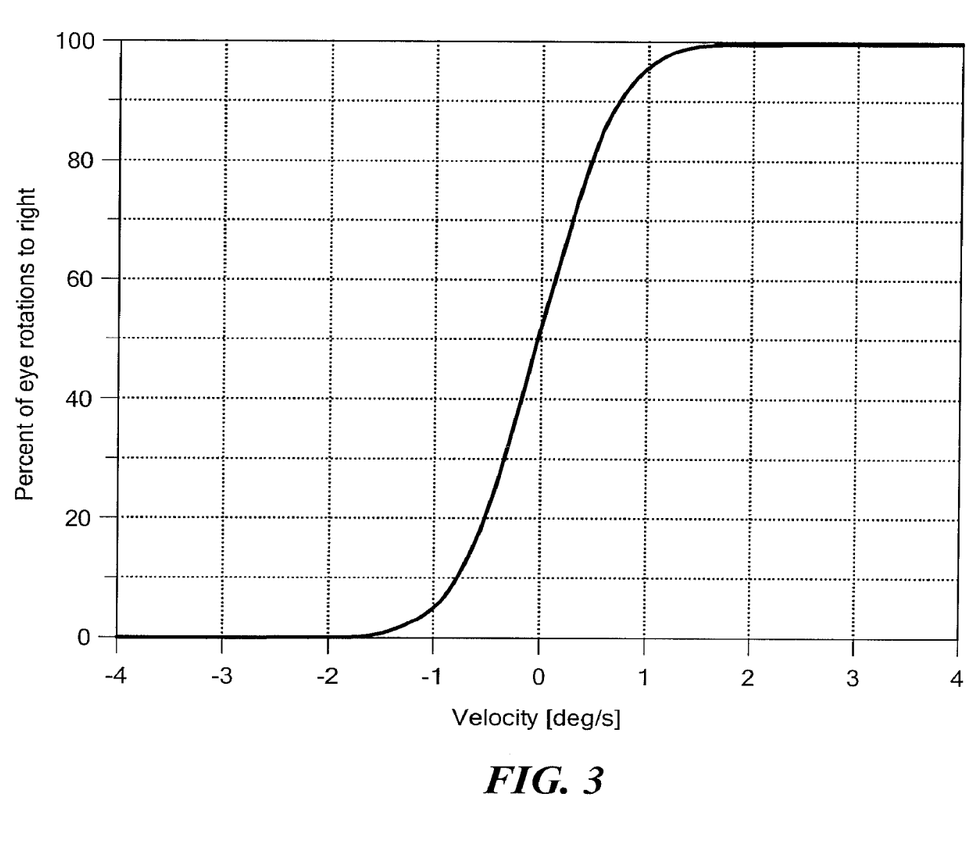
FIG. 3 shows a likelihood curve for different angular velocities.

The likelihood graph represented in FIG. 3 arose from causing a healthy subject 14 to experience 1 Hz motion with peak velocities ranging from −4 deg/sec to +4 deg/sec, with the data being fit with a normal cumulative distribution function using a generalized linear model. In such a case, the likelihood graph takes the shape of a sigmoid centered near the point (0 deg/sec, 50% likelihood). In some cases, the distribution of the vestibular noise may be something other than a normal distribution, such as a uniform distribution or a Poisson distribution, in which case the likelihood graph would have a correspondingly different shape.

It is apparent from FIG. 3 that when the patient is moved to the left with high velocity, (i.e. beyond about 2 deg/sec) the eye moves to the right (i.e. the correct direction) practically 100% of the time. On the other hand, when the velocity is near zero, there is relatively little vestibular stimulation, which means the eye has no reason to move in any preferred direction. As a result, eye motion when the velocity is near zero is dominated by random noise. In a normal subject 14, this would result in the eye moving in the correct direction 50% of the time. When the velocity is high but in the opposite direction, the eye moves to the right practically 0% of the time.

The slope of the sigmoid function depends on the amplitude of the vestibular noise, and therefore serves as another way to assay vestibular noise. The slope can thus be viewed as a characteristic of vestibular noise that can be used as a basis for assessing vestibular function. For example if the slope is small, such that the sigmoid does not reach the 100% level even with velocities as great as 4 deg/sec, it is reasonable to conclude that there exists a vestibular dysfunction, and in particular, a reduction in the sensitivity of the vestibular system to motion. Similarly, if the shape of the likelihood curve deviates significantly from the sigmoid, one can identify different problems on the basis of the overall shape of the likelihood curve. For example, a likelihood curve that lacks symmetry about the horizontal line at 50% likelihood might suggest greater sensitivity to motion in one direction than in the other. Other aspects of the likelihood curve may likewise be influenced by vestibular noise, and therefore be indicative of vestibular function. For example, the sigmoid shown in FIG. 3 may be shifted left or right, which would suggest a tendency for the subject to perceive a particular rotational speed as stationary.

In some practices, the quantity along the horizontal axis of FIG. 3 can represent some other characteristic of the motion besides velocity. Or it could be an abstract index that defines a particular set of motion parameters or a subset thereof. In either case, the VOR, and in particular the probability or likelihood that the VOR will have a particular characteristic, is used to assess vestibular function.

The motion used to generate the data summarized in FIG. 3 was a yaw rotation of an upright subject 14 about an earth-horizontal rotation axis. However, the technique, and devices implementing the technique, are not limited to such motions. For example, the techniques described herein can be used with pitch and roll, or with translation along a specified direction, or combinations thereof.

In a graph as shown in FIG. 3, the value of velocity at which the eye almost always moves to the correct direction can be viewed as a threshold for that particular motion profile. This value often varies from one subject to the next, possibly as a result of different vestibular noise levels in different subjects. For example, in FIG. 3, at a 1 Hz rotation, the particular subject 14 appears to correctly detect motion at least 90% of the time once the velocity exceeds about 0.8 deg/sec.

As used herein, "threshold" is not used in the sense of an absolute (e.g. mechanical) limit below which detection becomes impossible. Instead, "threshold" is used in a manner consistent with its use in signal detection theory to refer to a level at which signal can be recognized as being distinct from noise. In the context of perceptual threshold measurement, noise includes transduction noise, neural noise, noise applied intentionally, and noise incident to stimuli. In the case of VOR, noise includes oculomotor noise.

Figure 4:
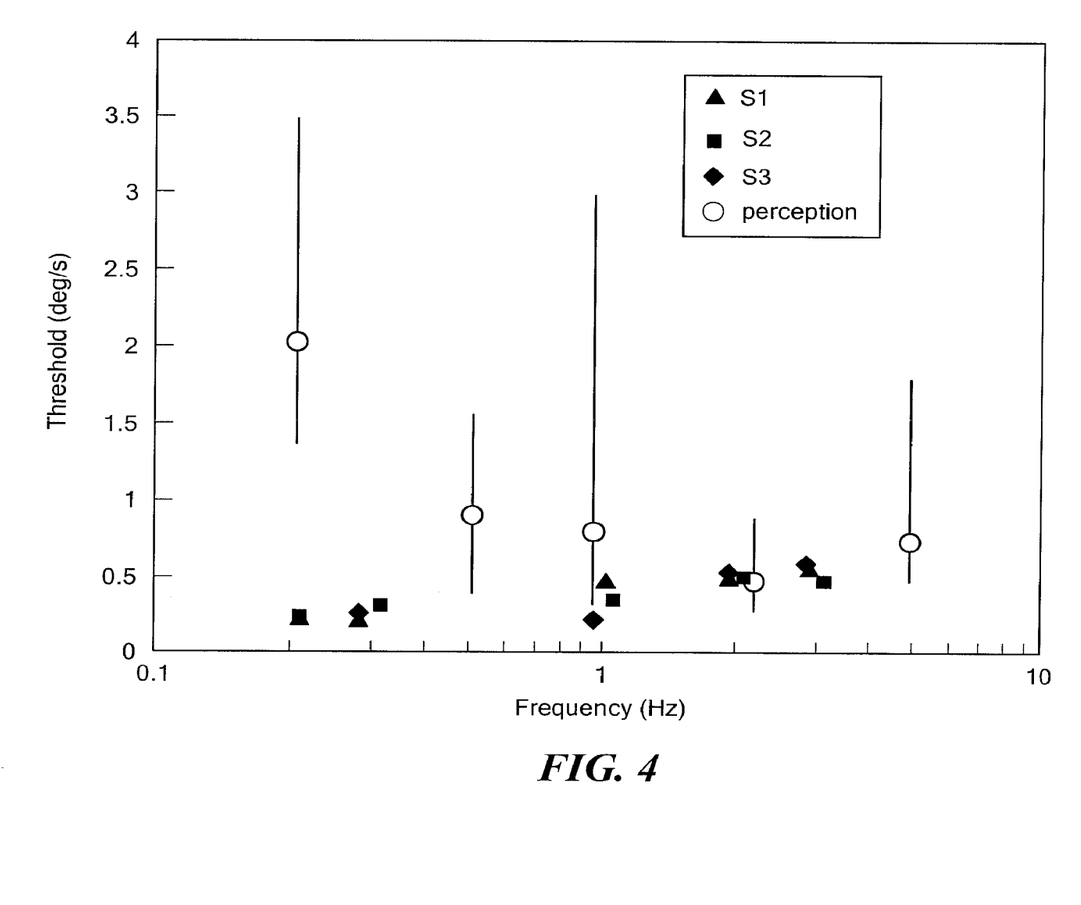
FIG. 4 shows a perception spectrum.

FIG. 4, compares measured VOR thresholds (filled symbols) with measured perceptual thresholds (open symbols) at different frequencies, including the 1 Hz frequency used in FIG. 3, together with an indication of the spread.

The filled symbols in FIG. 4 represent, for each of five selected frequencies, the angular velocity needed to detect VOR motion in a monkey undergoing motion at that frequency. Since three monkeys were used, there are three types of filled symbols. The open circle represents, for each of four selected frequencies, the average angular velocity at which human subjects were most likely to perceive motion at that frequency.

From FIG. 4, one can see that at 1 Hz, some subjects perceived motion as slow as 0.25 deg/sec and other subjects did not perceive motion until it reached 3 deg/sec, perhaps as a result of greater vestibular noise obscuring the vestibular signal. In contrast, at half that frequency (0.5 Hz), the same subjects had about the same 90% correct level at 1.0 Hz, but a much smaller spread. A perception spectrum such as that shown FIG. 4, with or without the spread shown at each frequency, is thus also influenced by vestibular noise and can be viewed as another characterization of vestibular noise that provides additional clues concerning the condition of the subject's vestibular system.

In the particular embodiment described herein, vestibular noise is assayed by stimulating the vestibular system and observing the resulting VOR. However, this pertains only to how vestibular noise is assayed, and not to the idea of using vestibular noise as a basis for vestibular diagnosis. Other methods of assaying vestibular noise can be used, some of which include measurement of signal relative to noise, others of which include assaying the noise itself, and others of which include indirectly assaying the vestibular noise by relying on patient perception.

For example, as shown in FIG. 4, one can measure perceptual thresholds as a function of frequency by having subjects provide subjective indications of their perception of motion. As another example, one can ask a subject to look straight ahead at a point source of light, such as an LED or point target on a computer. This measurement thus provides yet another way to assess vestibular noise. In particular, the variance or standard deviation of the resulting eye position and/or eye velocity can be quantified and compared to normative data.

Prior methods of using the VOR to assess vestibular function typically involve averaging measurements of VOR and using the average to assess vestibular function. In such cases, noise is undesirable and often filtered out. In contrast, in the methods described herein, the noise itself, and/or the measurement variability is a crucial part of the vestibular function assay.

Another method of assaying vestibular noise is to use variance of a distribution. For example, one can repeatedly subject a patient to motion, typically for a short duration, such as 0.1 seconds. The motion profile would be a single cycle of a sinusoid or trapezoid. For each such motion, one can measure the VOR. The result of each measurement would thus be a curve showing some characteristic of VOR over time.

Figure 5:
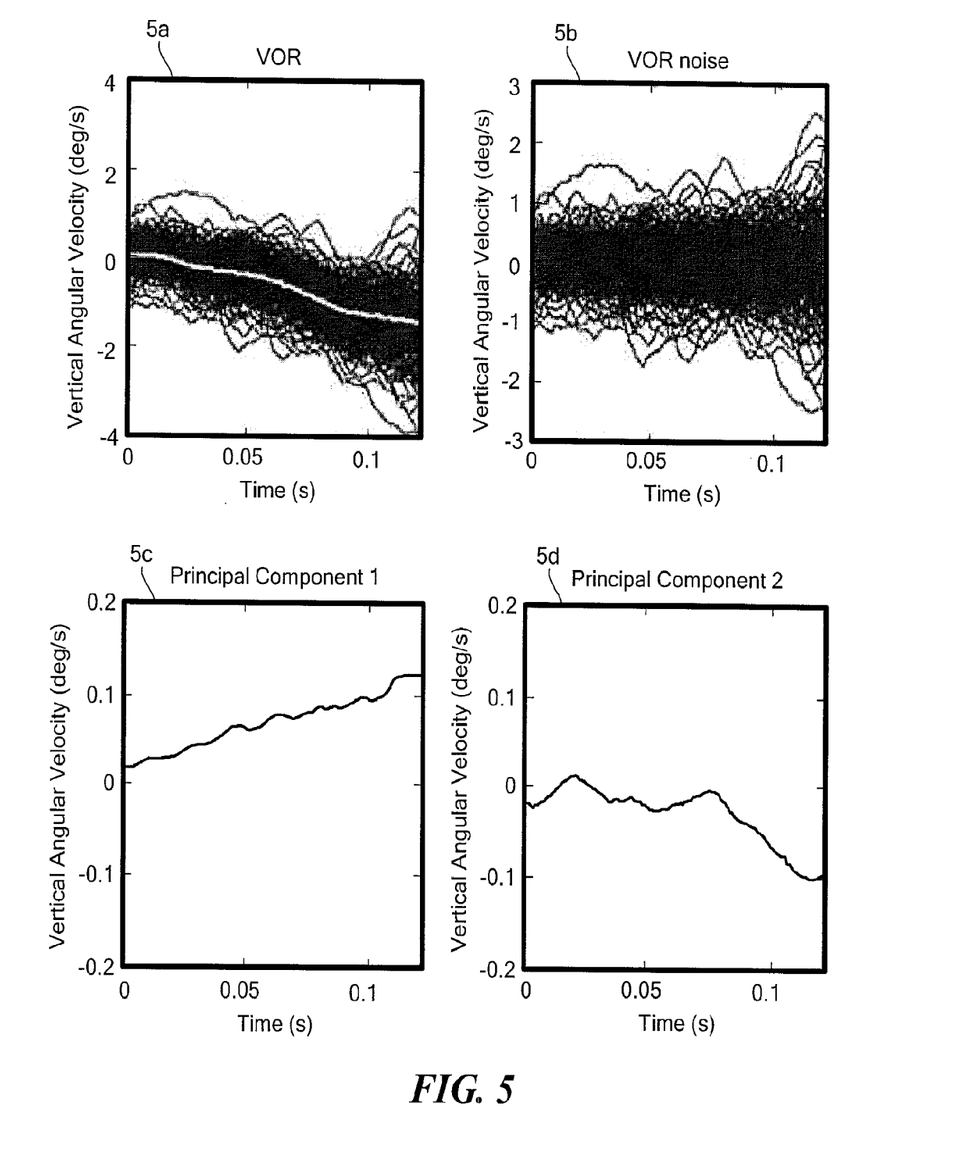
FIG. 5 shows steps in removal of principal components from data to expose underlying noise.

FIG. 5 suggests that noise and/or variability associated with VOR can be decomposed into principal components. The data shown in FIG. 5 arose from measuring vertical eye velocity in a non-human primate that has repeatedly experienced identical motions, each one being a single-cycle of a sinusoidally varying velocity profile, i.e. an acceleration sinusoid, with a frequency of 2 Hz and a peak velocity of 20 deg/sec. A similar analysis can be carried out for horizontal eye velocity.

The plot 5a shows angular velocity profiles of VOR for multiple motions, with the average profile overlaid in white. When this average motion is removed, the result is purely noise, as shown in plot 5b, which has its own noise average, noise variance, and noise spectrum.

Plots 5c and 5d show the first and second principal components as obtained by finding eigenvalues and eigenvectors of a covariance matrix made out of the time traces shown in plot 5b. Plot 5c suggests that the variance of the eye movement tends to increase with time or increase with velocity in a given trial.

While principal component analysis was carried out for plots 5c and 5d, a similar analysis could have been carried out using other related techniques that yield similar insights into response variability. One such technique is non-negative matrix factorization.

As suggested by plots 5e-5h, the principal components shown in plots 5c and 5d account for most of the variance caused by vestibular noise.

Plot 5f shows VOR noise that corresponds to the data shown in plot 5b, namely VOR data arising from observing VOR of a non-human primate undergoing motions. This noise can be compared with the noise shown in plot 5e, which arises from observing the VOR of a non-human primate staring fixedly at a target. Thus, the difference between the noise in plot 5e and 5f is believed to be noise caused by motion. Plot 5g shows the noise from plot 5f with variance arising from the first principal component removed. It is apparent that plot 5g begins to look similar to plot 5e. Plot 5h shows the noise from plot 5f but with variance arising from both principal components removed. It is apparent that plot 5h looks even more similar to plot 5e. This suggests that removal of the variance arising from the first two principal components removed VOR noise arising from motion, and hence noise related to vestibular stimulation.

Thus, as suggested by FIG. 5, the variance of noise obtained from VOR measurement of a moving subject can be used to characterize that portion of the noise that arises from the vestibular system. That noise variance can be extracted from the overall data by first removing the signal, thus leaving only noise. This noise is a mixture of vestibular noise and noise from all other pathways, including the instrumentation itself. Using principal component analysis, or forms of statistical analysis for analysis of variance, one can extract from this noise the variance associated with vestibular noise. The variance, represented in FIG. 5 by the first two principal components, is thus a characteristic of the vestibular noise that can be used in connection with predicting whether a vestibular disorder exists.

The methods described herein, in which vestibular noise is harnessed as an indicator of vestibular disease, can be used to detect the presence of a number of diseases, including, for example, bilateral vestibular hypofunction, unilateral vestibular loss, perilymphatic fistula, post-traumatic vertigo, Meniere's syndrome, migraine associated dizziness, Semicircular canal dehiscence, vestibular loss due to ototoxicity, and labyrinthitis.

Having described the invention, and a preferred embodiment thereof, what we claim as new, and secured by Letters Patent is:

The invention claimed is:

1. A method for providing information for predicting that a patient is afflicted by a vestibular disorder, the method comprising:
   causing a motion platform to execute a set of motions to stimulate a vestibular-ocular reflex (VOR) in a patient;
   measuring the VOR of the patient by generating a plurality of VOR measurements;
   assaying, based on the VOR measurements, one or more characteristics of vestibular noise that includes sensory noise originating in a vestibular system of the patient, wherein the one or more characteristics of the vestibular noise include a characteristic represented by a variability of the VOR measurements, the characteristic being indicative of a presence or absence of a disorder of the vestibular system; and
   at least in part on the basis of the one or more characteristics of the vestibular noise, providing information for predicting that the patient is afflicted by the disorder.

2. The method of claim 1, wherein measuring the VOR comprises measuring the VOR during patient movement.

3. The method of claim 1, wherein measuring the VOR comprises measuring the VOR while the patient stares fixedly at a visual target.

4. The method of claim 3, wherein measuring the VOR comprises measuring the VOR while the patient stares fixedly at a point source of light.

5. The method of claim 1, wherein assaying the one or more characteristics of the vestibular noise comprises receiving information indicative of the patient's perception of motion.

6. The method of claim 5, wherein the information indicative of the patient's perception of motion comprises information indicative of perceived direction of motion.

7. The method of claim 5, wherein the information indicative of the patient's perception of motion comprises information representing a selection from among at least two alternatives.

8. The method of claim 7, wherein the information representing a selection comprises information representing a selection from the group consisting of motion in a first direction and motion in a second direction.

9. The method of claim 7, wherein the information representing a selection comprises information representing a selection of an alternative selected from the group consisting of a perception of motion and a perception of motionlessness.

10. The method of claim 7, wherein the information representing a selection comprises information representing a selection from the group consisting of a first time interval and a second time interval, wherein a feature of interest occurs in the first time interval and the feature is absent from the second time interval.

11. The method of claim 7, wherein the information representing a selection comprises information representing a selection from the group consisting of a first time interval and a second time interval, wherein the motion in the first interval has a larger amplitude than the motion in the second interval.

12. The method of claim 7, wherein the information representing a selection comprises information representing a selection from the group consisting of a first time interval and a second time interval, wherein the motion in the first interval has a lower frequency than the motion in the second interval.

13. The method of claim 7, wherein the one or more characteristics of the vestibular noise includes a likelihood that the patient will perceive motion.

14. The method of claim 1, wherein the one or more characteristics of the vestibular noise includes a noise amplitude.

15. The method of claim 1, wherein the one or more characteristics of the vestibular noise includes a dependence of the vestibular noise on a frequency of the set of motions.

16. The method of claim 1, wherein the one or more characteristics of the vestibular noise includes a dependence of the patient's perception on a frequency of the set motions.

17. The method of claim 1, wherein:
the one or more characteristics of the vestibular noise include a likelihood that a particular motion of the set of motions will cause the patient to experience a VOR having a specified VOR characteristic, and
assaying the one or more characteristics of the vestibular noise includes estimating the likelihood based on the VOR measurements.

18. The method of claim 17, further comprising, for each motion of the set of motions, selecting the specified characteristic of the VOR to be movement of an eye in a direction opposed to a direction of said motion.

19. The method of claim 17, wherein causing the motion platform to execute the set of motions comprises causing the motion platform to execute a motion having a specified velocity profile and a specified duration.

20. The method of claim 17, wherein causing the motion platform to execute the set of motions comprises causing the motion platform to execute motions having random characteristics.

21. The method of claim 17, wherein causing the motion platform to execute the set of motions comprises causing the motion platform to execute motions having a sinusoidal velocity profile.

22. The method of claim 17, wherein providing the information for predicting that the patient is afflicted by the vestibular disorder comprises providing the information indicative of a slope of a curve that relates the likelihood with a characteristic of the particular motion.

23. The method of claim 17, wherein providing the information for predicting that the patient is afflicted by the vestibular disorder comprises providing information indicative of a shape of a curve that relates the likelihood with a characteristic of said particular motion.

24. The method of claim 17, wherein providing the information for predicting that the patient is afflicted by the vestibular disorder comprises providing information indicative of a bias in a curve that relates the likelihood with a characteristic of said particular motion.

25. The method of claim 17, wherein causing the motion platform to execute the set of motions comprises causing the motion platform to execute different motions at different frequencies, and wherein providing the information for predicting that the patient is afflicted by the vestibular disorder comprises providing the information indicative of a dependence of the vestibular noise on the different frequencies.

26. The method of claim 1, wherein the information for predicting that the patient is afflicted by the vestibular disorder includes information indicative of a variance of the measured VOR, the variance of the measured VOR being indicative of the presence or absence of the disorder.

27. The method of claim 1, wherein providing information for predicting that the patient is afflicted by the vestibular disorder comprises providing information for predicting that the patient is afflicted by a condition selected from a group consisting of: bilateral vestibular hypofunction, unilateral vestibular loss, perilymphatic fistula, post-traumatic vertigo, Meniere's syndrome, migraine associated dizziness, semicircular canal dehiscence, vestibular loss due to ototoxicity, and labyrinthitis.

28. A system comprising:
a motion platform configured to execute a set of motions;
a processor configured to:
  cause the motion platform to execute the set of motions to stimulate a vestibular-ocular reflex (VOR) in a patient;
  receive a signal indicative of the VOR of the patient;
  assay, based on the signal, one or more characteristics of vestibular noise that includes sensory noise originating in a vestibular system of the patient, wherein the one or more characteristics of the vestibular noise include a characteristic represented by a variability of the signal indicative of the VOR, the characteristic indicative of a presence or absence of a disorder of the vestibular system of the patient and
  at least in part on the basis of the one or more characteristics of the vestibular noise, provide information for predicting that a patient is afflicted by a vestibular disorder.

29. The method of claim 1, wherein measuring the VOR comprises:
using a VOR detector to detect an eye position of the patient while causing the motion platform to execute the set of motions, and
measuring the VOR based on the eye position.

30. The method of claim 1, wherein measuring the VOR comprises:
receiving a subjective indication of a perception of the patient to the set of motions, and
measuring the VOR based on the subjective indication.

31. The method of claim 1, wherein causing the motion platform to execute the set of motions comprises causing the motion platform to execute a motion having a near zero velocity.

32. The method of claim 1, further comprising diagnosing the patient with the vestibular disorder based on the information for predicting the patient is afflicted with the vestibular disorder.

33. A method for providing information for predicting that a patient is afflicted by a vestibular disorder, the method comprising:
using a vestibular-ocular reflex (VOR) detector to detect an eye position of the patient;

measuring the VOR based on the eye position by generating a plurality VOR measurements;

assaying, based on the VOR measurements, one or more characteristics of vestibular noise that includes sensory noise originating in a vestibular system of the patient, wherein the one or more characteristics of the vestibular noise include a characteristic represented by a variability of the VOR measurements, the characteristic being indicative of a presence or an absence of a disorder of the vestibular system of the patient; and at least in part on the basis of the one or more characteristics of the vestibular noise, providing information for predicting that a patient is afflicted by the disorder.

34. The method of claim 1, wherein the variability of the VOR measurements is calculated by removing, from the measured VOR, an average of the VOR measurements.

35. The method of claim 1, wherein assaying the one or more characteristics of the vestibular noise includes extracting the characteristic of the vestibular noise from the variability of the VOR measurements.

36. The method of claim 35, wherein the variability of the VOR measurements includes the vestibular noise originating in the vestibular system of the patient and noise originating in instrumentation for measuring the VOR.

* * * * *

UNITED STATES PATENT AND TRADEMARK OFFICE
CERTIFICATE OF CORRECTION

| | |
|---|---|
| PATENT NO. | : 9,681,835 B2 |
| APPLICATION NO. | : 13/885263 |
| DATED | : June 20, 2017 |
| INVENTOR(S) | : Faisal Karmali, Csilla Haburcakova and Daniel Michael Merfeld |

Page 1 of 1

It is certified that error appears in the above-identified patent and that said Letters Patent is hereby corrected as shown below:

In the Specification

Column 1, Lines 14-16, delete "government support under Grant R01-DC 04158 awarded by NIH/NIDCD. The government has certain rights in the invention." and insert --government support under Grant Number DC004158 awarded by the National Institutes of Health. The government has certain rights in this invention.--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*